(12) United States Patent
Mairel

(10) Patent No.: US 9,456,610 B2
(45) Date of Patent: Oct. 4, 2016

(54) PLANT EXTRACTS FOR USE AS PHYTOCHEMICALS

(75) Inventor: François Mairel, Vouvray (FR)

(73) Assignee: IDENA S.P.A., Milan (IT)

( * ) Notice: Subject to any disclaimer, the term of this patent is extended or adjusted under 35 U.S.C. 154(b) by 1249 days.

(21) Appl. No.: 13/130,813

(22) PCT Filed: Nov. 3, 2009

(86) PCT No.: PCT/EP2009/007866
§ 371 (c)(1),
(2), (4) Date: Jul. 18, 2011

(87) PCT Pub. No.: WO2010/060528
PCT Pub. Date: Jun. 3, 2010

(65) Prior Publication Data
US 2012/0121742 A1 May 17, 2012

(30) Foreign Application Priority Data

Nov. 25, 2008 (EP) .................................. 08169837

(51) Int. Cl.
*A61K 36/87* (2006.01)
*A61K 36/00* (2006.01)
*A01N 65/00* (2009.01)
*A01N 65/08* (2009.01)

(52) U.S. Cl.
CPC ............... *A01N 65/00* (2013.01); *A01N 65/08* (2013.01)

(58) Field of Classification Search
None
See application file for complete search history.

(56) References Cited

U.S. PATENT DOCUMENTS

| 2007/0036871 | A1* | 2/2007 | Westerman et al. | 424/661 |
| 2007/0134354 | A1 | 6/2007 | Angeletti et al. | |
| 2009/0098227 | A1* | 4/2009 | Neifeld et al. | 424/769 |
| 2009/0156484 | A1* | 6/2009 | Valenti et al. | 514/12 |
| 2009/0202667 | A1* | 8/2009 | Giori et al. | 424/766 |

FOREIGN PATENT DOCUMENTS

| CN | 101298397 A | * | 11/2008 |
| EP | 0 348 781 A | | 1/1990 |
| FR | 2 092 743 A | | 1/1972 |
| WO | 2004/062370 A | | 7/2004 |
| WO | 2005/036988 A | | 4/2005 |
| WO | 2006/016383 A | | 2/2006 |
| WO | 2007/017037 A | | 2/2007 |

* cited by examiner

*Primary Examiner* — Chris R Tate
*Assistant Examiner* — Randall Winston
(74) *Attorney, Agent, or Firm* — Silvia Salvadori, P.C.; Silvia Salvadori

(57) ABSTRACT

The invention concerns the use of grape (*Vitis vinifera*) seeds extracts as agents for the treatment and prevention of plant diseases caused by pathogens, particularly by fungi and oomycetes, as well as fungicidal compositions comprising *Vitis vinifera* extracts for application to plants affected or liable to be affected by a pathogen, especially a fungus or oomycete.

3 Claims, No Drawings

PLANT EXTRACTS FOR USE AS PHYTOCHEMICALS

This application is a U.S. national stage of PCT/EP2009/007866 filed on Nov. 3, 2009 which claims priority to and the benefit of Italian Application No. EP 08169837.5 filed on Nov. 25, 2008, the contents of which are incorporated herein by reference.

The present invention concerns the use of grape (*Vitis vinifera*) seeds extracts as agents for the treatment and prevention of plant diseases caused by pathogens, particularly by fungi and oomycetes.

The invention accordingly provides fungicidal compositions comprising *Vitis vinifera* extracts for application to plants affected or liable to be affected by a pathogen, especially a fungus or oomycete.

BACKGROUND OF THE INVENTION

A number of plant diseases caused by pathogens such as fungi, moulds, oomycetes, bacteria and viruses are known. Many of them, usually connected with climatic conditions favouring their onset and diffusion, have dramatic consequences, causing losses of yields of crops which may have a deep and sometimes catastrophic impact on agricultural economy, especially when the disease assumes the epidemic status.

An historically remarkable example of a plant disease causing devastating consequences is the potato infection (late blight) by *Phytophthora infestans* responsible for the great Irish famine of in the late 1840s.

Another oomycete, *Plasmopara viticola*, is responsible for the so called downy mildew, one of the most widespread infections affecting, causing huge damages to wine producers and grape growers, negatively affecting the yield as well as the quality of production.

A similar grapevine disease, called powdery mildew, is caused by the fungus *Erysiphe necator*, also known as *Uncinula necator*.

Similar infections affect other plants such as soybean, sunflower, lettuce, tomato, potato, oaks, ornamental plants, fruit plants, tobacco, cucurbits.

A comprehensive review on plant disease is reported in the European Handbook of Plant Diseases, ed. by I. M. Smith et al., 1988, Blackwell Scientific Publications.

Several natural and synthetic agents have been proposed and are available for treating the above mentioned plant diseases.

In addition to sulfur and copper salts or complexes, synthetic fungicides for agrochemical use belong to very broad and different chemical classes (phenylamides, benzimidazole derivatives, dicarboximides, carbamates, carbanilates, dithiocarbamates, dinitroanilines, etc.). The use of said synthetic agents is limited by the well known phenomenon of resistance as well as by the toxic effects which may be induced by said agents in humans and animals and by their environmental pollution potential.

Research efforts are therefore being paid for developing more environment-friendly fungicides, possibly of natural origin, which may possibly substitute the known synthetic fungicides or at least which may be used in combination with them in order to reduce the resistance phenomenon and/or their environmental impact.

Several oils such as cinnamon essential oil, rosemary oil and neem oil are known as effective fungicides.

U.S. Pat. No. 6,174,920 discloses moreover the use of jojoba wax for controlling powdery mildew infections.

Jojoba extract has also been reported as a pre-treatment to prevent powdery mildew infection on grape plants in CA 2,103,014 whereas US 2007/0071831 discloses a product for the prevention and/or treatment of infections obtained by the partial or total neutralization of lees deriving from winemaking processes.

WO 2006/006878 discloses a fungicidal composition comprising anhydrous fat milk optionally in combination with one or more of soybean oil, olive oil and coconut oil.

DESCRIPTION OF THE INVENTION

It has now been found that extracts of *Vitis vinifera* seeds or marcs containing seeds are effective in the control of plant pathogens, particularly of fungi and oomycetes.

The invention accordingly provides phytopharmaceutical compositions comprising an extract of *Vitis vinifera* seeds or marcs containing seeds as the active ingredient.

The invention has a very deep interest for the worldwide economy by the new valorisation given by reusing wastes of wineries before further existing valorisations as oil recovery, distillation, heat production by burning the biomass or composting which are always possible after the extraction.

The compositions of the invention are useful for the treatment and/or prevention of infections by pathogenic organisms of plants including grapevine and other crop plants liable to be infected by said pathogens.

The invention also concerns a method for preventing or treating plant infections by fungi or oomycetes comprising the application of an effective amount of *Vitis vinifera* seeds or marcs containing seeds extract on the plant to be treated.

Experimental tests reported below have shown a remarkable activity of *Vitis vinifera* seeds extracts against two of the most common pathogens of grapevine, namely *Plasmopara viticola* and *Erysphe necator*. However, it should be understood that the invention is not limited to the treatment of grapevine infections by these two pathogens only, being rather applicable to a variety of other fungi and oomycetes affecting other plants of interest.

The following is a list of exemplary pathogens affecting plants of interest.

1—Oidium
*Erysiphe necator=Uncinula necator* (Grape)
*Erysiphe graminis* (Cereals)
*Podosphaera leucotricha* (Tree crops, Fruit trees)
*Sphaerotheca pannosa* (Rose plants)
2—Mildews
*Plasmopara viticola* (Grape)
*Plasmopara helianthi* (Sunflower)
*Phytophthora infestans* (Potato)
*Phytophthora parasitica* (Tomato)
3—Fruit Trees Scab
*Venturia inaequalis* (Apple tree)
*Venturia pirina* (Pear tree)
4—Peach Leaf Curl
*Taphrina deformans*
5—Septoriosis
*Septoria nodorum* and *Septoria tritici* (Cereals)
*Septoria* sp. (Colza)
6—Rusts
*Puccinia graminis, Puccinia recondita* and *Puccinia striiformis* (Cereals)
7—Smut Disease
*Ustilago tritici* (Wheat)
*Ustilago maydis* (Maize)
*Ustilago hordei* (Barley)
8—Bunt

*Tilletia tritici, Tilletia caries* and *Tilletia foetida* (Cereals)
9—Collar Rot
*Phoma lingam* (Crucifers, Colza)
*Rhizoctonia solani* (Potato)
*Sclerotinia sclerotiorum* (Tomato)
10—Anthracnose
*Colletotrichum gloeosporioides* (Pea)
*Colletotrichum lindemuthianum* (Bean)
11—Grey mould
*Botrytis cinerea* (Grape)

Particularly interesting is the effect of the extracts of the invention against the pathogens listed under 1, 2, 3, 4, 9, 10 and 11.

An example of another pathogen which can be effectively controlled by *Vitis vinifera* extract is for instance *Phytophthora infestans*, infecting various members of the Solanaceae, such as potato, tomato and some ornamentals.

The extracts of *Vitis vinifera* seeds or marcs containing seeds according to the invention may be prepared by extracting and purifying the fresh or dried seeds or marcs containing seeds with different solvents such as water, acetone, ethyl acetate, ethanol, butanol or mixtures thereof, under different extraction parameters and technologies.

Many extracts are known and commercially available. For instance, a grape seed extract obtained by extraction with a water-ethanol mixture is disclosed in WO 2007/017037.

The use of solvents such as water and ethanol is of course preferable in view of the low cost and low toxicity of these solvents. It has been also found that an extract particularly suited for use according to the present invention may be obtained by a process comprising:

extraction of grape seeds with hot water;
removal of the water-insoluble fraction;
purification on adsorption resin column;
concentration;
spray-drying.

The extract obtainable by said process has a content of catechin and epicathechin from 5 to 30% (HPLC), a total content of polyphenols ranging from 90 to 110% (Folin-Ciocalteau's spectrophotometric method). Said extract is new and is a further object of the invention.

The *Vitis vinifera* seeds extracts may be used as such, suitably dissolved or suspended in a carrier suited for application on the plant, or they may be formulated in combination with suitable excipients, such as for example wetting additives, adjuvant, or with other active ingredients, e.g. known fungicides, copper compounds, oils and the like.

The amount of *V. vinifera* seed extract in the composition may range from 5 to 25 g/liters but this range could be adjust in function of the said composition, the pathogen to treat, the plant to protect and the treatment technology.

The composition may be administered to the plant by any suitable technique, for instance by spraying with conventional devices and the treatment may be carried out weekly or according to a time sequence which will be decided by the grower depending on several factors such as climatic conditions, extent of infection, virulence of the infecting organism, use of other phytochemicals and the like.

As an ex-ample, in the case of affected by downy mildew, the *Vitis vinifera* seed extract will be typically sprayed on and under the leaves in an amount ranging from 0.1 to 10 grams per plant and per treatment, every one to three weeks, from early spring until late summer, even until the harvest period. The exact amount will of course depend on the plant density which is very variable in function of the geographic area and of the variety of vine: for example around 3000 plant/ha in Tuscany, around 7500 plant/ha in Champagne or around 10000 plant/ha in Burgundy. Furthermore, the total "ready to use" solution volume sprayed on plants could vary in function of the product and the technology: from 300 to 750 liters/ha, equivalent to 5 g/l×300 l/ha/10000 plants/ha=0.15 g/plant up to a maximum of 25 g/l×750 l/ha equivalent to 3000 plant/ha=6.25 g/plant.

The invention is illustrated in more detail in the following examples.

Example 1

Preparation of a Water Extract of *Vitis Vinifera* Seeds: VITIVAC 1000 g of dried grape seeds are covered with hot water at 75° C. For 4 hours in a jacketed static percolator or in jacketed reactor equipped with stirrer.

Then the biomass is percolated with hot water at 75° C., the recovered percolate is discharge in continuous until a total volume of 7.5 liters. The percolation flow is ideally around 1 liter per hour.

The total recovered percolates are cooled to 20° C. and filtered to eliminate fine particles with a 50 microns filter.

The water solution is then loaded in continuous by the top of a chromatographic column containing 1 liter of Rhom and Haas AMBERLITE®XAD 7HP resin or equivalent previously regenerated and filled with water. The conductivity of the water exiting in the bottom of the column is followed.

At the end of the fixation step, the resin is rinsed with ideally 4 liters of water and then eluted in continuous with ideally 4 liters of 70% v/v ethanol and consecutively rinse again with 4 liters of water. The conductivity of the water exiting in the bottom of the column is followed.

The resulting ethanolic solution is collected, concentrated under vacuum and washed with water to eliminate ethanol.

The solution is then concentrated under vacuum and spray dried at temperature below 85° C.

The obtained powder is mixed, controlled and packaged in airtight and opaque bags.

The standard yield is 93 g corresponding to a yield on the starting material of 9.30% w/w. But this yield could vary in function of the biomass used.

This product has a catechin (cathechin+epicatechin) HPLC content of 8.5% and a total polyphenols content of 98%.

Example 2

Fungicidal Activity of *Vitis Vinifera* Seeds Extract: VITIVAC

Plants s of *Vitis vinifera* cv. Chardonnay were used to study the effect of fungicides on downy mildew. Plants were grown from the seeds (one plant per 0.1-1 pot) and put in a growth chamber (23° C. day/19° C. night, 100-120 $\mu E \cdot m^{-2} \cdot s^{-1}$, 16 h light per day). Seedlings were fertilized twice weekly with 0.1 liter of a 0.2 g/l of N-P-K fertilizer (20-20-20). Eight-week old seedlings with at least four fully developed leaves were used for studying the biological activity of VITIVAC.

Pathogen

An isolate of *Plasmopara viticola* Pv1, obtained in 2007 from infected plants in a vineyard located in the Champagne region, France, was maintained onto detached surface-disinfected leaves of "Chardonnay". The leaves were placed in Petri dishes and put in a growth chamber (23° C. day/19° C. night, 100-120 $\mu E \cdot m^{-2} \cdot s^{-1}$, 16 h light per day). The inoculum was obtained from freshly sporulating leaves 8-12 days after inoculation. Sporangia were suspended in 4° C. distilled water and adjusted with the aid of a haemocytometer to a concentration of $5 \times 10^5$ sporangia·ml$^{-1}$ of water.

Fungicide Treatments

The natural product, prepared as described in example 1 (VITIVAC), was used at a rate of 25 g/l throughout the experimentation. The efficacy of VITIVAC was compared to that of the reference fungicide mixture of Fosetyl-Al (500 g/kg)+Folpel (250 g/kg) used at a rate of 4.0 kg of formulated product/ha (Mikal Flash WG, Bayer CropScience).

Surface disinfected leaves of "Chardonnay" were placed, abaxial side up, in 14 cm diameter plastic Petri dishes each containing a filter paper, moistened with 8 ml of water. The leaves were sprayed using a laboratory sprayer (Euro-Pulvé) equipped with one cone nozzle (Teejet XR 110015 VS) with an air pressure of 2 bars. Fungicide preparations were applied in a volume of 400 and 720 l·ha$^{-1}$ for Mikal Flash and VITIVAC, respectively. Each test was replicated 3 times. Data were analyzed statistically by using the Newman-Keuls test (XLS-Stat, Addinsoft).

Treated leaves were placed under laminar flow for 30 min in order to dry the fungicide applied on the abaxial face of the leaves. After drying, Petri dishes containing treated or untreated (control) leaves were kept in a growth chamber (23° C. day/19° C. night, 100-120 µE·m$^{-2}$·s$^{-1}$, 16 h light per day) for 24 hours.

Inoculation with *Plasmopara Viticola*

Ten leaf disks (each 10 mm in diameter) were cut with a cork borer from each treated or untreated (control) leaves and placed, abaxial side up, in 9 cm diameter plastic Petri dishes containing filter paper, moistened with 4 ml of sterile distilled water. Disks were inoculated by placing one drop (20 µl) of inoculum ($5 \times 10^5$ sporangia·ml$^{-1}$). After inoculation, the Petri dishes containing 10 leaf disks were incubated at 19° C. for 24 h in darkness and were then kept in a growth chamber (23° C. day/19° C. night, 100-120 µE·m$^{-2}$·s$^{-1}$, 16 h light per day) for disease development. At the end of the experiment, the Petri dishes were kept at 19° C. for 24 h in darkness, to induce sporulation.

Ten days after the inoculation, the number of leaf disks exhibiting downy mildew development was determined for each modality tested (frequency of infection). Then, downy mildew lesions accompanied by whitish sporangia were rated according to a 0-4 scale, as previously described by Reuveni (Relationship between leaf age, peroxidase and b 1-3 glucanase activity and resistance to downy mildew in s, 1998. *Journal of Phytopathology* 146, 525-530): 0, no lesions; 1, 1-10% of the leaf disk area infected and sporulating; 2, 11-25%; 3, 26-50%; and 4, >50% (intensity of the infection). The numbers of sporangia produced on leaf disks were estimated. Sporangia were washed from 10 leaf disks in a known volume of sterile distilled water containing 0.01% Tween 80, and counted with the aid of a haemocytometer (six counts per 10 leaf disks). The number of sporangia produced per square centimeter of leaf disk area was calculated (intensity of the sporulation). The experiment was conducted once, with three Petri dishes for each treatment.

| Terms of treatment | *Plasmopara viticola* (1) Observation 10 days after inoculation | | |
|---|---|---|---|
| | Infection$^\alpha$ frequency (effectiveness % of Te) | Infection$^\beta$ intensity (effectiveness % of Te) | Sporulation intensity (sporocyctes/cm$^2$) (effectiveness % of Te) |
| Reference solution | 1 +/- 0 | 2.6 +/- 0 | $3.22 \cdot 10^5$ +/- $0.60 \cdot 10^5$ |
| ITV1 | 0.5 +/- 0.1 (50%) | 1.1 +/- 0.2 (58%) | $0.75 \cdot 10^5$ +/- $0.30 \cdot 10^5$ (77%) |
| ITV2 | 0.5 +/- 0 (50%) | 0.65 +/- 0.05 (75%) | $1.21 \cdot 10^5$ +/- $0.03 \cdot 10^5$ (62%) |
| Extract according to US 2007/0071831 | 0.7 +/- 0 (30%) | 1.4 +/- 0.1 (46%) | $1.84 \cdot 10^5$ +/- $0.33 \cdot 10^5$ (43%) |
| Lieboost | 0.7 +/- 0.1 (30%) | 1.25 +/- 0.15 (52%) | $1.07 \cdot 10^5$ +/- $0.14 \cdot 10^5$ (67%) |
| VITIVAC | 0 +/- 0 (100%) | 0 +/- 0 (100%) | 0 +/- 0 (100%) |
| Mikal | 0 +/- 0 (100%) | 0 +/- 0 (100%) | 0 +/- 0 (100%) |

$^\alpha$Infection frequency: Number of contaminated inoculated disks/total number of disks (10).
$^\beta$Infection intensity: Arbitrary scale (from 0 to 4) representative of infection intensity of each leaves disk.

The results are reported in the following Table.

Similar favourable results were obtained by treating leaves infected by *Erysiphe necator*. The procedure was substantially the same, except that the infection by *Erysiphe necator* was induced by shaking contaminated leaves over the Petri dishes. In this case, the treatment of the invention proved particularly effective in reducing the sporulation intensity, defined as number of conidia (*P. viticola*) per surface unit (cm$^2$).

The following are examples of phytopharmaceutical compositions.

Example 3

| *Vitis vinifera* extract | g | 250 |
|---|---|---|
| Soquabiol ® | ml | 200 |
| Deionized water | l | 100 |

Example 4

| *Vitis vinifera* extract | g | 500 |
|---|---|---|
| Sticman ® | ml | 40 |
| Deionized water | l | 100 |

The invention claimed is:

1. A method for preventing or treating plant infections by fungi or oomycetes comprising the application of an effective amount of *Vitis vinifera* seeds extract on a plant to be treated.

2. A method according to claim 1, wherein the plant is *Vitis vinifera*.

3. A method according to claim 2, wherein the plant infections are caused by *Plasmopara viticola*.

\* \* \* \* \*

UNITED STATES PATENT AND TRADEMARK OFFICE
CERTIFICATE OF CORRECTION

| | |
|---|---|
| PATENT NO. | : 9,456,610 B2 |
| APPLICATION NO. | : 13/130813 |
| DATED | : October 4, 2016 |
| INVENTOR(S) | : Mairel |

It is certified that error appears in the above-identified patent and that said Letters Patent is hereby corrected as shown below:

On the Title Page

Column 1, item (73) Assignee, reads:
IDENA S.P.A., Milan (IT)

Should read:
"INDENA S.P.A., Milan (IT)"

Signed and Sealed this
Twenty-first Day of February, 2017

Michelle K. Lee
*Director of the United States Patent and Trademark Office*